US00PP28445P2

(12) United States Plant Patent
Hurd

(10) Patent No.: US PP28,445 P2
(45) Date of Patent: Sep. 26, 2017

(54) ***PEROVSKIA* PLANT NAMED 'DENIM 'N LACE'**

(50) Latin Name: ***Perovskia atriplicifolia* (Benth.)**
Varietal Denomination: Denim 'n Lace

(71) Applicant: Kevin A. Hurd, Austin, TX (US)

(72) Inventor: Kevin A. Hurd, Austin, TX (US)

(73) Assignee: Walters Gardens, Inc., Zeeland, MI (US)

( * ) Notice: Subject to any disclaimer, the term of this patent is extended or adjusted under 35 U.S.C. 154(b) by 14 days.

(21) Appl. No.: 14/998,972

(22) Filed: Mar. 10, 2016

(51) Int. Cl.
*A01H 5/00* (2006.01)

(52) U.S. Cl.
USPC ..... Plt./226

(58) Field of Classification Search
USPC ..... Plt./226, 263.1
See application file for complete search history.

*Primary Examiner* — Susan McCormick Ewoldt

(57) ABSTRACT

The new and distinct cultivar of ornamental, hardy, Russian Sage plant, *Perovskia* 'Denim 'n Lace' with short, tight compact, upright habit of strong erect stems, long flowering season of large, densely-arranged, lavender-blue flowers on short branched stems. Foliage is silvery-green, highly-dissected, pinnately-compound with serrated margins and is retained well and keeps its color throughout the growing season.

1 Drawing Sheet

Botanical classification: *Perovskia atriplicifolia* (Benth.).
Variety denomination: 'Denim 'n Lace'.

BACKGROUND OF THE INVENTION

The present invention relates to a new and distinct plant of Russian sage, botanically known as *Perovskia atriplicifolia* 'Denim 'n Lace' and will be referred to hereinafter also by its cultivar name 'Denim 'n Lace' and the new plant. The new plant cultivar of *Perovskia* is a hardy herbaceous perennial grown for landscape use.

*Perovskia* 'Denim 'n Lace' is from the selection of seed from *Perovskia atriplicifolia* 'LISSLITT' U.S. Plant Pat. No. 20,845 collected by the inventor Kevin A. Hurd in the summer of 2010 at a nursery in Zeeland, Mich. All subsequent evaluations were performed in a full-sun trial garden at the same nursery with loamy sand soil and irrigation and fertilizer as required. The single seedling plant was selected for further evaluation during the summer of 2012 and given the breeder designation "K10-01-03." The plant was propagated by stem cuttings at the same nursery in Zeeland, Mich. and the original plant and the cuttings evaluated over the next two years until final approval for introduction in the summer of 2014. The resultant asexually propagated cuttings have been stable and identical to the original plant in successive asexual propagations.

No plants of *Perovskia* 'Denim 'n Lace' have been sold in this country, or anywhere in the world, prior to the filing of this application, nor has any disclosure of the new plant been made prior to the filing of this application with the exception of that which was disclosed within one year of the filing of this application and was derived either directly or indirectly from the inventor.

SUMMARY OF THE INVENTION

*Perovskia atriplicifolia* 'Denim 'n Lace' differs from its parent as well as all other hardy Russian sage known to the inventor in a combination of traits. The following characteristics in combination distinguish 'Denim 'n Lace' from all other *Perovskia* plants known to the inventor:

1. Short, compact, tight and upright habit with erect strong stems;
2. Long flowering season of large, densely-arranged, lavender-blue flowers on short branched stems;
3. Silvery-green, highly-dissected, pinnately compound and serrated foliage retained throughout growing season.

The nearest comparison plants are the parent plant *Perovskia* 'LISSLITT' U.S. Plant Pat. No. 20,845, 'Peek-a-Blue' (not patented), and 'Rocketman' U.S. Plant Pat. No. 27,526. Compared to cultivar 'LISSLITT', *Perovskia* 'Denim 'n Lace' has a more upright tighter habit, and the foliage is more dissected. Compared to 'Peek-a-Blue' the new plant has denser more upright branches and coarser leaf divisions and is less prone for foliage to turn yellow and drop lower leaves. Compared to 'Rocketman', *Perovskia* 'Denim 'n Lace' has a shorter habit with shorter branching, more dissected foliage and earlier flowering. In comparison to 'Crazy Blue' U.S. Plant Pat. No. 25,639, the new plant has denser, more closely clustered flowers and denser habit.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plant used in the photograph is a three-year old plant grown in full sun field in loamy sand soil in trial gardens of a nursery in Zeeland, Mich.

DETAILED BOTANICAL DESCRIPTION

Figure 1:
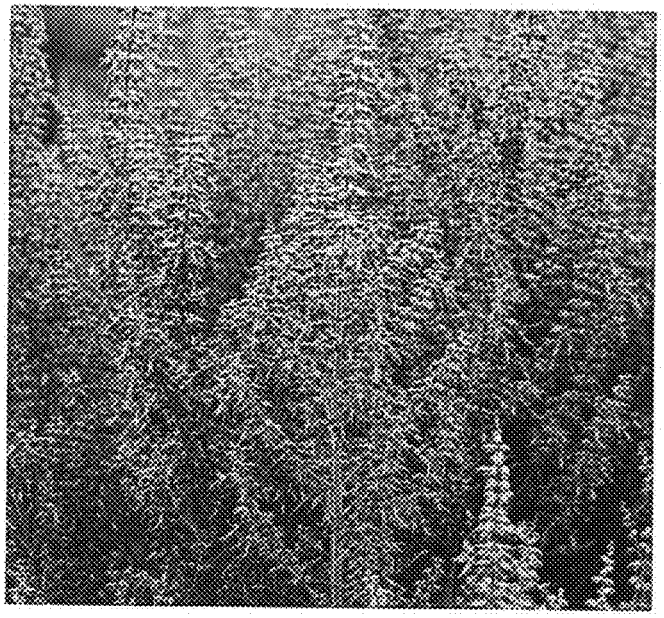
FIG. 1 shows a close-up of the flower stems of 'Denim 'n Lace' in the landscape.
Figure 2:
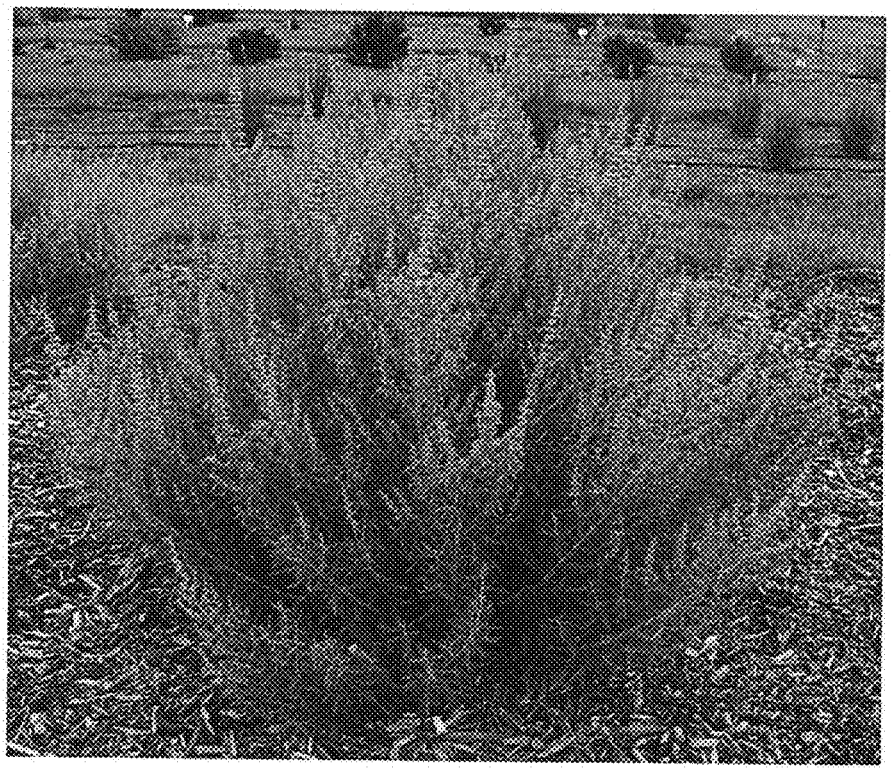
FIG. 2 shows a of the landscape habit of 'Denim 'n Lace'.

The following is a detailed description of *Perovskia atriplicifolia* 'Denim 'n Lace' as observed and compared to other cultivars for three years in trial gardens and production fields at a nursery in Zeeland, Mich. The following description is of a three-year old plant of *Perovskia atriplicifolia* 'Denim 'n Lace' in a full-sun display garden in Zeeland, Mich. with limited supplemental fertilizer and irrigation as needed and without any pinching or plant growth regulators. The new plant has not been observed under all possible environments, and the phenotype may vary slightly with different environmental conditions, such as temperature, light, fertility, moisture and maturity levels, but without any change in the genotype. The color descriptions are in accordance with The 2001 edition of The R.H.S. Colour Chart of The Royal Horticultural Society, London, England, except where common dictionary color terms are used.

Plant habit: Upright and dense shape; oppositely branched; deciduous, semi-woody sub-shrub usually dying to the ground in most Michigan winters and re-sprouting with new stems from the base each spring; about 64 stems per plant.

Plant size: About 85.0 cm in height, average stem height of about 80.0 cm, and about 85.0 cm in width about 40 cm above soil.

Root description: Fibrous; color nearest RHS 155D.

Propagation: Stem cuttings; root initiation occurs in about 14 days at a temperature of 20° C.

Growth rate: Moderately vigorous.

Crop time: About 12 to 14 weeks to produce flowering plant from rooted plug.

Stem description: Quadangular; oppositely branched; young portions lanulose; older stems becoming woody at base; average about 80.0 cm long and about 7.0 mm across near base; about 36 branches per stem; with herbal fragrance.

Stem color: Nearest RHS 191D.

Internode length: Average 2.7 cm.

Internode color: Same as surrounding stem.

Branches: Quadangular; opposite; lanulose; average about 50° angle above horizontal; lower branches about 25.0 cm long and about 2.5 mm diameter, decreasing distally to upper branches about 6.0 cm long and about 1.0 mm diameter.

Branch color: Nearest RHS 191D.

Foliage description: Opposite, broadly ovate, deeply palmately cleft, acute apex and broadly acute base; serrate, farinose on abaxial and puberulent on adaxial surface; about 8.0 cm long and about 3.5 mm wide, shorter in distal region, average about 6.0 cm long and about 2.0 cm wide; with herbal fragrance.

Leaf color: Adaxial nearest RHS 138A; abaxial between RHS 138A and RHS 138B.

Leaf venation: Pinnate.

Vein color: Main adaxial vein between RHS 147D and RHS 148D; abaxial main vein between RHS 147C and RHS 147D.

Petiole: Flattened abaxial to adaxial; slightly concavo-convex; to about 18.0 mm long and about 2.0 mm across, average about 9.0 mm long and about 1.7 mm across at stem.

Petiole color: Adaxial between RHS 147D and RHS 148D; abaxial between RHS 147D and RHS 147C.

Inflorescence: Main stems vertical, branched verticillate panicle; about 10.0 cm tall above last branch and about 2.5 cm across; total inflorescence portion average about 60.0 cm tall and about 9.0 cm wide.

Flower buds about one day prior to opening: About 10.0 mm long and about 2.0 mm wide; long ovoid; rounded apex; rounded base; calyx abaxial with dense long pubescence about 1.0 mm long.

Bud color: Calyx hairs nearest RHS N82C; adaxial calyx nearest RHS 86A with veins of nearest RHS 187A, abaxial calyx between RHS 83C and 83D with undertone of between RHS 146D and RHS 147C and veins of nearest RHS 86A; extended unopened petal portion nearest RHS 96B.

Flowers: Bilabiate with upper and lower lip fused in about basal 6.5 mm; zygomorphic; about 14.0 mm long and about 6.0 mm across; face opening to nearly flat; up to 15 flowers per verticil and over 600 per main stem; individual flowers open for about 4 days.

Flower attitude: Outward and slightly downward.

Fragrance: Slight herbal.

Flowering season: Beginning about mid-July in Michigan and remaining effective for about eight weeks.

Corolla: Glabrous abaxial, puberulent in adaxial throat; bilabitate; upper lip four-lobed, each with rounded apex and about 2.0 mm across and about 2.0 mm long, together measuring about 6.0 mm across; lower lip entire with obtuse apex; nearly flat, about 6.0 mm long and about 4.0 mm wide at fusion point; base fused into tube; tube about 8.5 mm in length and about 2.5 mm in width.

Corolla color: Distal upper and lower lips adaxial nearest RHS N94A, distal one half of fused lips nearest RHS 92C and proximal one half of fused lips nearest RHS 92D; distal upper and lower abaxial nearest RHS 94B with the distal one half of fused tube lighter than RHS 94D and proximal one half of tube lighter than RHS 92D.

Gynoecium: One pistil.

*Style*.—About 7.0 mm long and less than about 0.5 mm wide; color of base white, lighter than RHS 155D and distal about 1.0 mm nearest RHS N77C.

*Stigma*.—Splitting into two in the terminal 0.5 mm; color nearest RHS 155B.

Androecium: Four, in two sets, two longer and fertile and two shorter and sterile; stamens adnate to corolla.

*Filaments* (*fertile pair*).—Exsected about 2.0 mm beyond lower lip; about 8.0 mm in length and less than about 0.5 mm in width; color nearest RHS 155D at base and gradually developing to nearest RHS 83D toward apex.

*Filaments* (*sterile pair*).—Fused to upper lip, about 3.0 mm long and less than 0.5 mm diameter; color nearest RHS 155D at base and nearest RHS 83D in about apical 0.5 mm.

*Anther*.—Fertile pair elliptic; about 1.0 mm long and 0.5 mm across, versatile; color nearest RHS N92B; sterile pair flattened ovoid, about 0.5 mm long and about 0.3 mm diameter; color nearest RHS 85C.

*Pollen*.—Abundant on fertile anthers; color nearest RHS 11D.

Calyx: Tubular campanulate; about 6.0 mm long and about 2.5 mm across; made up of five sepals fused at base in the proximal about 5.0 mm with apical about 1.0 mm separate; entire, apex acute; outside densely pubescent and glandular, inside glabrous; persistent for weeks after flower abscission and drop.

Calyx color: Abaxial color at flowering and after between RHS 83C and RHS 83D with overtones of between RHS 146D and RHS 147C and veins nearest RSH 86A and hairs between RHS 85B and RHS 85A; adaxial color nearest RHS 147D with veins nearest RHS 187A.

Seed: Ovoid to spatulate in outline; about 2.0 mm long and about 1.0 mm diameter; color nearest RHS 200D.

*Hardiness to at least U.S.D.A. zones* 4 *to* 9.—The new plant is very resistant to drought once established and even tolerant of clay soils if good drainage is provided.

*Pest and disease resistance*.—Russian sage is typically resistant to deer and rodent browsing. The new plant is less prone to yellowing foliage and lower leaf drop than other known Russian sage cultivars. No other susceptibility or resistance to diseases or pests has been observed except that which is common to *Perovskia.*

I claim:

1. A new and distinct cultivar of hardy Russian sage plant, *Perovskia* 'Denim 'n Lace' as herein described and illustrated.

* * * * *